United States Patent
Jeong et al.

(10) Patent No.: US 9,474,404 B2
(45) Date of Patent: Oct. 25, 2016

(54) COOKING APPARATUS AND METHOD OF CONTROLLING THE SAME

(71) Applicant: SAMSUNG ELECTRONICS CO., LTD., Suwon-si (KR)

(72) Inventors: Yong Won Jeong, Seoul (KR); Soo Jung Lee, Gimpo-si (KR); Seong Hun Ahn, Incheon (KR); Young Chul Ko, Suwon-si (KR); Mu Kun An, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/334,840

(22) Filed: Jul. 18, 2014

(65) Prior Publication Data

US 2015/0182058 A1 Jul. 2, 2015

(30) Foreign Application Priority Data

Dec. 30, 2013 (KR) ........................ 10-2013-0166979

(51) Int. Cl.
| | |
|---|---|
| *A47J 43/28* | (2006.01) |
| *A47J 27/62* | (2006.01) |
| *G01N 33/12* | (2006.01) |
| *H05B 6/64* | (2006.01) |
| *H05B 6/68* | (2006.01) |
| *A23L 1/01* | (2006.01) |

(Continued)

(52) U.S. Cl.
CPC *A47J 27/62* (2013.01); *A23L 1/01* (2013.01); *A47J 36/00* (2013.01); *F24C 7/08* (2013.01); *G01N 33/12* (2013.01); *H05B 6/6447* (2013.01); *H05B 6/687* (2013.01); *A23V 2002/00* (2013.01)

(58) Field of Classification Search
CPC ........ A23L 1/01; A47J 27/62; H05B 6/6447; H05B 6/87; F24C 15/16; G01N 33/12
USPC ........................................... 99/342
See application file for complete search history.

(56) References Cited

U.S. PATENT DOCUMENTS

| | | | | |
|---|---|---|---|---|
| 5,549,041 | A | * | 8/1996 | Zhang ................... A23L 3/32 99/451 |
| 6,242,714 | B1 | * | 6/2001 | Narumiya .............. G01K 7/343 219/385 |

(Continued)

FOREIGN PATENT DOCUMENTS

| | | |
|---|---|---|
| DE | 10 2009 026957 A1 | 12/2010 |
| DE | 10 2009 047013 A1 | 5/2011 |

(Continued)

OTHER PUBLICATIONS

Machine translation of DE 10 2009 026 957 A1, Bauer et al, Dec. 23, 2010.*

(Continued)

*Primary Examiner* — Dana Ross
*Assistant Examiner* — Lindsey C Teaters
(74) *Attorney, Agent, or Firm* — Staas & Halsey LLP

(57) ABSTRACT

A cooking apparatus including an impedance measurer that measures impedance of an object to be heated by applying electricity to a first electrode portion and a second electrode portion that contact an outer side of the object to be heated and that are spaced apart from each other by a predetermined distance and a controller that determines a cooking state of the object to be heated based on the measured impedance.

16 Claims, 27 Drawing Sheets

(51) Int. Cl.
*A47J 36/00* (2006.01)
*F24C 7/08* (2006.01)

(56) References Cited

U.S. PATENT DOCUMENTS

| | | | | |
|---|---|---|---|---|
| 6,875,958 B2* | 4/2005 | Soavi | ............ | H05B 6/6452 |
| | | | | 219/413 |
| 6,914,226 B2* | 7/2005 | Ottaway | ............ | A21B 2/00 |
| | | | | 219/775 |
| 7,459,920 B2* | 12/2008 | Mizukami | ............ | G01N 27/048 |
| | | | | 324/444 |
| 2002/0072318 A1* | 6/2002 | Long | ............ | A22C 9/00 |
| | | | | 452/141 |
| 2002/0173041 A1* | 11/2002 | Canas | ............ | G01N 33/12 |
| | | | | 436/21 |
| 2004/0097180 A1* | 5/2004 | Long | ............ | A22C 9/00 |
| | | | | 452/141 |
| 2006/0174775 A1* | 8/2006 | Yitzchak | ............ | F24C 7/087 |
| | | | | 99/358 |
| 2012/0169354 A1* | 7/2012 | Erbe | ............ | G01N 33/02 |
| | | | | 324/649 |
| 2012/0310541 A1* | 12/2012 | Katz | ............ | G01N 27/06 |
| | | | | 702/19 |
| 2014/0287112 A1* | 9/2014 | Hukelmann | ............ | A23L 3/005 |
| | | | | 426/244 |

FOREIGN PATENT DOCUMENTS

EP    1 253 423 A2    10/2002
EP    2 299 261 A1    3/2011

OTHER PUBLICATIONS

European Search Report dated May 8, 2015 issued in corresponding European Patent Application 14178379.5.
Decision on Grant dated Mar. 9, 2016 issued in corresponding European Patent Application 14 178 379.5.

* cited by examiner

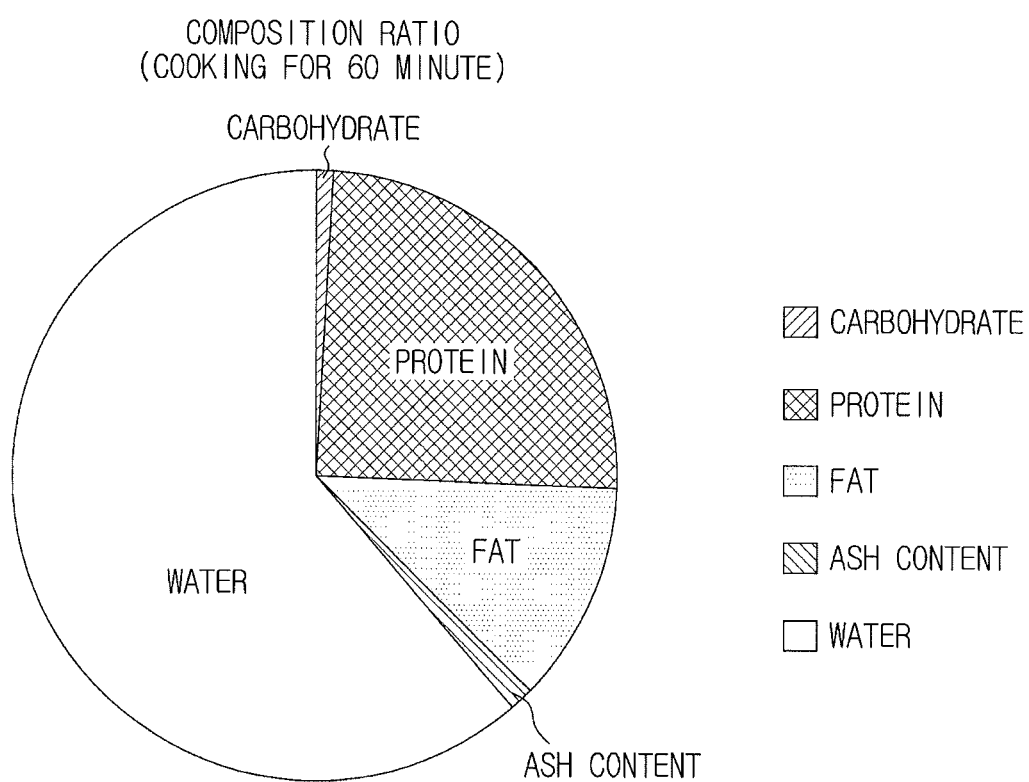

FIG. 18A

|  | TEMPERATURE | IMPEDANCE RELATIVE VALUE (RELATIVE VALUE COMPARED TO INITIAL VALUE) | PASSAGE OF INFLECTION POINT |
|---|---|---|---|
|  |  | 1.000 | X |
| rare | 60°C | 0.420 | X |
| medium-rare | 65°C | 0.435 | O |
| medium | 70°C | 0.450 | O |
| medium-well done | 75°C | 0.475 | O |
| well done | 80°C | 0.500 | O |

FIG. 18B

|  | TEMPERATURE | IMPEDANCE RELATIVE VALUE (RELATIVE VALUE COMPARED TO INITIAL VALUE) | PASSAGE OF INFLECTION POINT |
|---|---|---|---|
| INITIAL STAGE |  | 1.000 | X |
| COOKED | 80°C | 0.500 | O |

FIG. 18C

|  | TEMPERATURE | IMPEDANCE RELATIVE VALUE (RELATIVE VALUE COMPARED TO INITIAL VALUE) | PASSAGE OF INFLECTION POINT |
|---|---|---|---|
| INITIAL STAGE |  | 1.000 | X |
| COOKED | 85°C | 1.500 | O |
| COOKED, BROWNISH | 90°C | 2.500 | O |

COOKING APPARATUS AND METHOD OF CONTROLLING THE SAME

CROSS-REFERENCE TO RELATED APPLICATIONS

This application claims the benefit of Korean Patent Application No. 10-2013-0166979, filed on Dec. 30, 2013 in the Korean Intellectual Property Office, the disclosure of which is incorporated herein by reference.

BACKGROUND

1. Field

Embodiments of the present disclosure relate to a cooking apparatus that cooks an object to be heated, and a method of controlling the cooking apparatus.

2. Description of the Related Art

Cooking apparatuses are apparatuses that cook food by heating food that is an object to be heated. Such cooking apparatuses may be classified as various products, such as ovens or microwave ovens, according to a method of heating food.

Since these cooking apparatuses cook the object to be heated, by generating heat according to a heat-dissipating amount set for a predetermined amount of time that is set by a user, the user of a cooking apparatus cannot accurately recognize a cooking progress state of the object to be heated.

SUMMARY

Therefore, it is an aspect of the present disclosure to provide a cooking apparatus that is capable of determining a cooking state of an object to be heated, and a method of controlling the cooking apparatus.

Additional aspects of the disclosure will be set forth in part in the description which follows and, in part, will be obvious from the description, or may be learned by practice of the disclosure.

In accordance with one aspect of the present disclosure, a cooking apparatus includes: a first electrode portion and a second electrode portion that contact an outer side of an object to be heated and that are spaced apart from each other by a predetermined distance; an impedance measuring unit that measures impedance of an object to be heated by applying electricity to a first electrode portion and a second electrode portion that contact an outer side of the object to be heated and that are spaced apart from each other by a predetermined distance; and a controller that determines a cooking state of the object to be heated based on the measured impedance.

The impedance measuring unit may include: a voltage source that applies a voltage having a predetermined electric frequency to the object to be heated; and an amperemeter that detects a current applied to the object to be heated.

The impedance measuring unit may include: a current source that applies a current having a predetermined electric frequency to the object to be heated; and a voltmeter that detects a voltage applied to the object to be heated.

The first electrode portion may include a plurality of first electrodes that are electrically connected to each other, and the second electrode portion may include a plurality of second electrodes that are electrically connected to each other.

The cooking apparatus may further include an impedance database in which impedance of the object to be heated according to the cooking state is stored.

The impedance database may store additional factors according to the cooking state. The additional factors may include at least one selected from the group consisting of passage of an inflection point in which impedance decreases and increases again, temperature of the object to be heated, and temperature of a cooking chamber.

The controller may search the impedance database for a cooking state corresponding to the measured impedance.

The controller may normalize the measured impedance, may convert the impedance into normalized impedance, and may determine a cooking state of the object to be heated based on the normalized impedance. The normalized impedance may be converted based on impedance of the object to be heated measured in a cooking initial state.

The controller may finish cooking of the object to be heated when the cooking state is a preset cooking state.

The cooking apparatus may further include a holder that includes the first electrode portion and the second electrode portion and supports the object to be heated.

The first electrode portion and the second electrode portion may be electrically connected to the impedance measuring unit.

The holder may include: a first holder that includes the first electrode portion and contacts an upper portion of the object to be heated; a second holder that includes the second electrode portion and supports a lower portion of the object to be heated; and a connection member that connects the first holder and the second holder so that the first holder can move.

The holder may include: an upper plate portion that includes the first electrode portion and the second electrode portion and has a plurality of through holes formed therein; and a housing that has an opening formed in one side thereof, the upper plate portion being accommodated in the opening, and that accommodates foreign substances discharged through the plurality of through holes.

The impedance measuring unit may measure a plurality of pieces of impedance of the object to be heated at different electric frequencies, and the controller may determine a cooking state of the object to be heated based on the plurality of impedance of the object to be heated.

In accordance with another aspect of the present disclosure, a method of controlling a cooking apparatus includes: measuring impedance of an object to be heated by applying electricity to a first electrode portion and a second electrode portion that contact an outer side of the object to be heated and that are spaced apart from each other by a predetermined distance; and determining a cooking state of the object to be heated based on the measured impedance.

The measuring of the impedance may include: applying a voltage or current having a predetermined frequency to the object to be heated and measuring a current or voltage applied to the object to be heated.

The determining of the cooking state may include: normalizing the measured impedance and converting the impedance into normalized impedance; and searching an impedance database for the cooking state corresponding to the normalized impedance.

The method may further include: receiving a cooking state of the object to be heated from a user; and if the cooking state of the object to be heated is the cooking state input from the user, finishing cooking

BRIEF DESCRIPTION OF THE DRAWINGS

These and/or other aspects of the disclosure will become apparent and more readily appreciated from the following description of the embodiments, taken in conjunction with the accompanying drawings of which:

FIGS. 6A through 6D illustrate a body composition ratio that varies as cooking of the object to be heated proceeds;

FIGS. 18A through 18C are views for describing an impedance database in accordance with an embodiment of the present disclosure;

DETAILED DESCRIPTION

Figure 1:
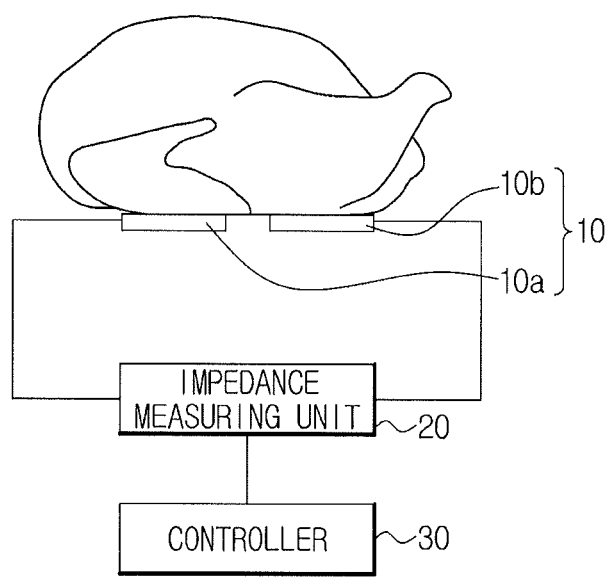
FIG. 1 is a control block diagram for describing an apparatus for measuring a cooking state in accordance with an embodiment of the present disclosure.

Reference will now be made in detail to the embodiments of the present disclosure, examples of which are illustrated in the accompanying drawings, wherein like reference numerals refer to like elements throughout.

FIG. 1 is a control block diagram for describing an apparatus for measuring a cooking state in accordance with an embodiment of the present disclosure.

Referring to FIG. 1, an apparatus 1 for measuring a cooking state includes an impedance measuring unit 20 for measuring impedance of an object to be heated that contacts an electrode portion 10, and a controller 30 for determining a cooking state of the object to be heated based on measured impedance. In this case, the object to be heated may be food to be cooked, for example, meat or fish.

The impedance measuring unit 20 measures impedance of the object to be heated. To this end, the impedance measuring unit 20 may apply a current or voltage with a predetermined frequency to the object to be heated according to control of the controller 30 and may measure the voltage or current applied to the object to be heated. In detail, the impedance measuring unit 20 may apply fine electricity, e.g., a low current, to an electrode portion 10 including a first electrode portion 10$a$ and a second electrode portion 10$b$ that are spaced apart from each other by a predetermined distance and that are electrically opened. In this case, the first electrode portion 10$a$ and the second electrode portion 10$b$ may be electrically connected to each other via the object to be heated.

Also, the voltage or current measured by the impedance measuring unit 20 may be transferred to the controller 30, and the controller 30 may calculate impedance of the object to be heated based on a value of the voltage or current measured by the impedance measuring unit 20. Meanwhile, the impedance measuring unit 20 may calculate impedance of the object to be heated and may transfer a value of the calculated impedance to the controller 30. Hereinafter, the impedance measuring unit 20 will be described with reference to FIGS. 2 through 4 in more detail.

Figure 2:
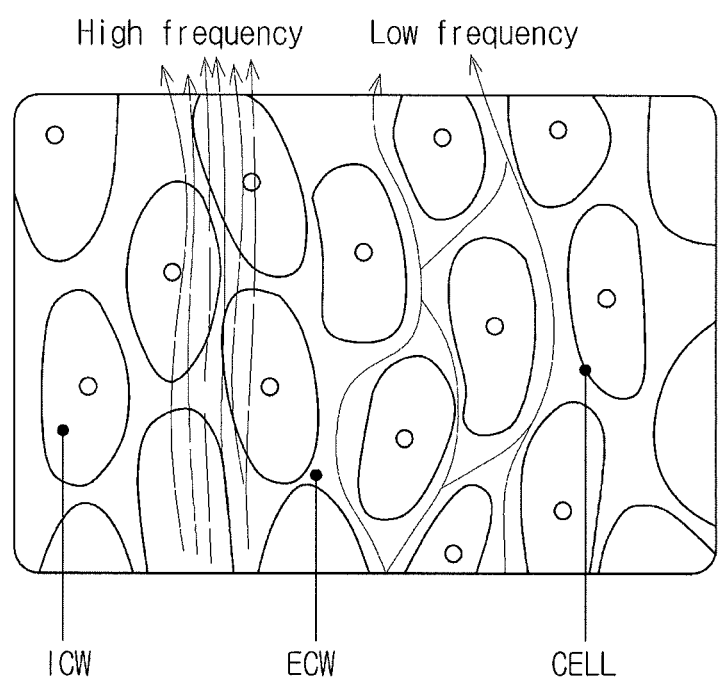
FIG. 2 illustrates an example of a tissue diagram of an object to be heated, for describing impedance of the object to be heated.
Figure 3:
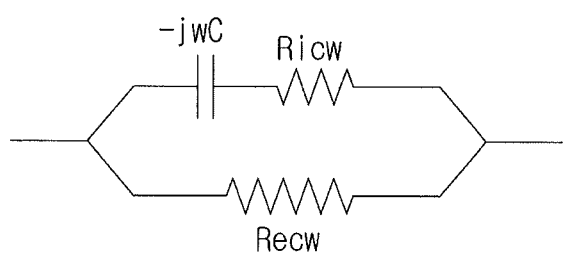
FIG. 3 illustrates an example of a circuit that is configured by modeling the object to be heated.

FIG. 2 illustrates an example of a tissue diagram of an object to be heated, for describing impedance of the object to be heated, and FIG. 3 illustrates an example of a circuit that is configured by modeling the object to be heated.

Although the object to be heated that will be cooked is configured of a plurality of tissues, the object to be heated may be simply classified as cells surrounded by cell membranes and water that exits in tissues, as illustrated in FIG. 2. In this case, water may be segmentalized as intracellular water (ICW) that exits in cell membranes and extracellular water (ECW) that exists between cells.

The object to be heated may be modeled as one circuit illustrated in FIG. 3. In detail, water that constitutes the object to be heated is a homogeneous conductor. Thus, the whole part of ECW may be modeled as one resistance component $R_{ecw}$. Meanwhile, a direct current (DC) does not flow through the cell membranes but an alternating current (AC) having a relatively high electric frequency flows better through the cell membranes. Thus, the cell membranes included in the tissues may be modeled as a capacitor component C, and ICW may be modeled as a resistance component $R_{icw}$ that is connected in series with a capacitor, and impedance of the object to be heated may be expressed as the following Equation 1.

$$Z = R_{ecw} // (R_{icw} + j \cdot w \cdot C) \quad \text{[Equation 1]}$$

$$= \frac{R_{ecw} \cdot (R_{icw} \cdot (R_{icw} + R_{ecw}) + (w \cdot C)^2)}{(R_{icw} + R_{ecw})^2 + (w \cdot C)^2} -$$

$$j \frac{w \cdot R_{ecw}^2 \cdot C}{(R_{icw} + R_{ecw})^2 + (w \cdot C)^2}$$

$$= R_{eq} - j \cdot X_{eq}$$

Impedance of the object to be heated is expressed in Equation 1, where Z is impedance of the object to be heated, and $R_{ecw}$ is a resistance component caused by ECW, and $R_{icw}$ is a resistance component caused by ICW, and w is an electric frequency applied to the object to be heated, and C is a reactance component caused by the cell membranes. Also, $R_{eq}$ is a resistance component of impedance of the object to be heated, and $X_{eq}$ is a reactance component of impedance of the object to be heated.

Impedance Z of the object to be heated may be calculated by the voltage and current applied to the object to be heated. In detail, impedance of the object to be heated may be calculated by the Ohm's law (Z=V/I). Thus, the impedance measuring unit 20 may apply a predetermined voltage or current to the electrode portion 10 and may measure a current or voltage applied to the circuit so as to calculate impedance of the object to be heated.

Figure 4:
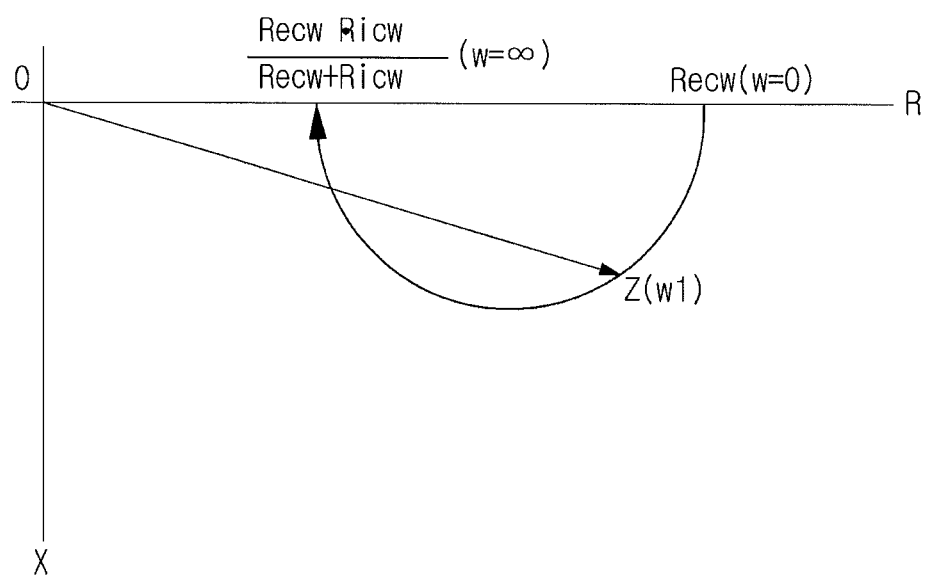
FIG. 4 illustrates a complex locus showing a change in impedance of the object to be heated versus a change in electric frequency.

FIG. 4 illustrates a complex locus showing a change in impedance of the object to be heated versus a change in electric frequency. As illustrated in FIG. 4, impedance of the object to be heated may vary according to electric frequencies of the voltage and current applied to the object to be heated. That is, as an electric frequency applied to the object to be heated increases, the size of impedance of the object to be heated increases and then decreases.

Figure 5A:
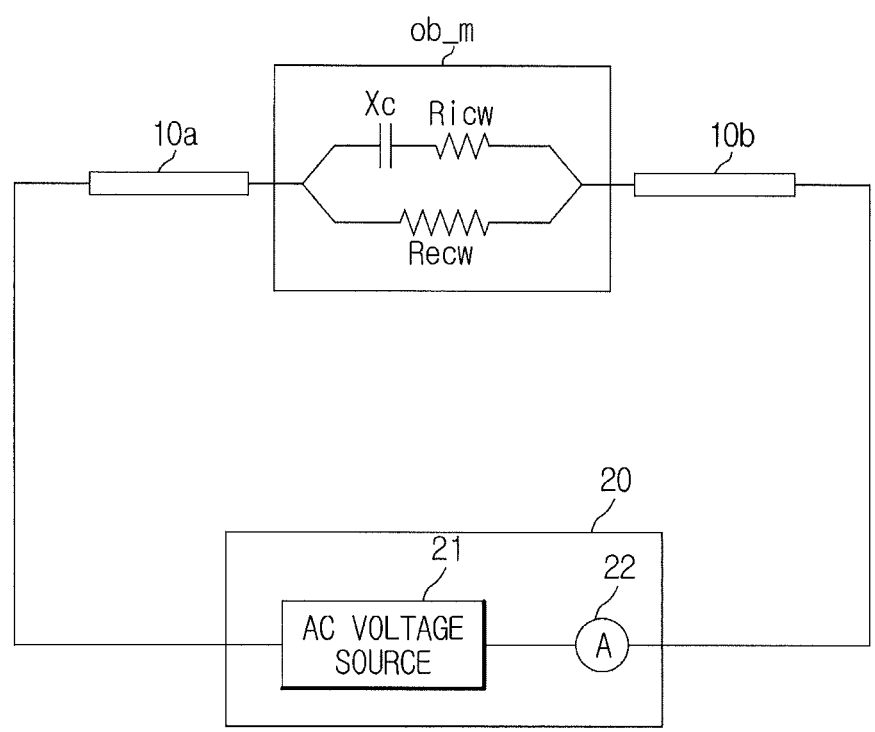
FIGS. 5A and 5B schematically illustrate application examples of an impedance measurement unit in accordance with an embodiment of the present disclosure.
Figure 5B:
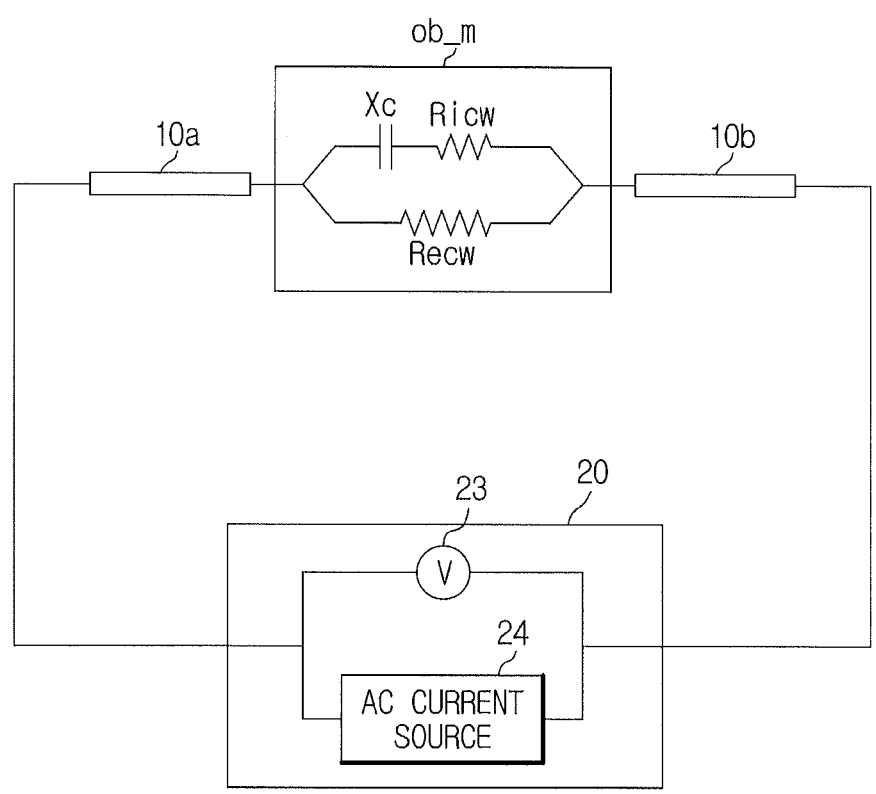

FIGS. 5A and 5B schematically illustrate application examples of an impedance measurement unit in accordance with an embodiment of the present disclosure. When the object to be heated is converted into a circuit ob_m modeled in FIG. 3, as described above and is displayed, it may be simply displayed that the modeled circuit ob_m is connected to the first electrode portion 10a and the second electrode portion 10b, as illustrated in FIGS. 5A and 5B.

The impedance measuring unit 20 may include a power supply unit that applies electricity to the object to be heated and a detector that detects the voltage or current applied to the object to be heated. For example, the impedance measuring unit 20 may include an AC voltage source 21 that applies an AC voltage having a predetermined frequency to the object to be heated that contacts the first electrode portion 10a and the second electrode portion 10b, and an amperemeter 22 that measures a current flowing through the object to be heated, as illustrated in FIG. 5A. In this case, the electric frequency of the AC voltage applied by the AC voltage source 21 to the object to be heated may be controlled by the controller 30, and the amperemeter 22 measures a current flowing through the circuit ob_m. Impedance of the object to be heated may be calculated based on the voltage applied by the AC voltage source 21 and the current measured by the amperemeter 22.

Also, the impedance measuring unit 20 may include an AC current source 24 that applies an AC current having a predetermined electric frequency to the object to be heated that contacts the electrode portion 10, and a voltmeter 23 that measures a voltage applied to the object to be heated. In this case, the electric frequency of the AC current applied by the AC current source 24 to the object to be heated may be controlled by the controller 30, and impedance of the object to be heated may be measured based on the current applied by the AC current source 24 to the object to be heated and the voltage measured by the voltmeter 23.

Meanwhile, FIGS. 5A and 5B illustrate an application example of the impedance measuring unit 20, and embodiments of the present disclosure are not limited thereto. The impedance measuring unit 20 may be implemented as various circuits for measuring impedance of the object to be heated and may include a configuration for correcting impedance generated by a conducting wire that connects the electrode portion 10 and the impedance measuring unit 20.

The controller 30 may determine a cooking state of the object to be heated based on impedance of the object to be heated measured by the impedance measuring unit 20. Meanwhile, the controller 30 may calculate impedance of the object to be heated based on a value of the current or voltage measured by the impedance measuring unit 20. Hereinafter, the controller 30 will be described with reference to FIGS. 6 through 8 in more detail.

Figure 6A:
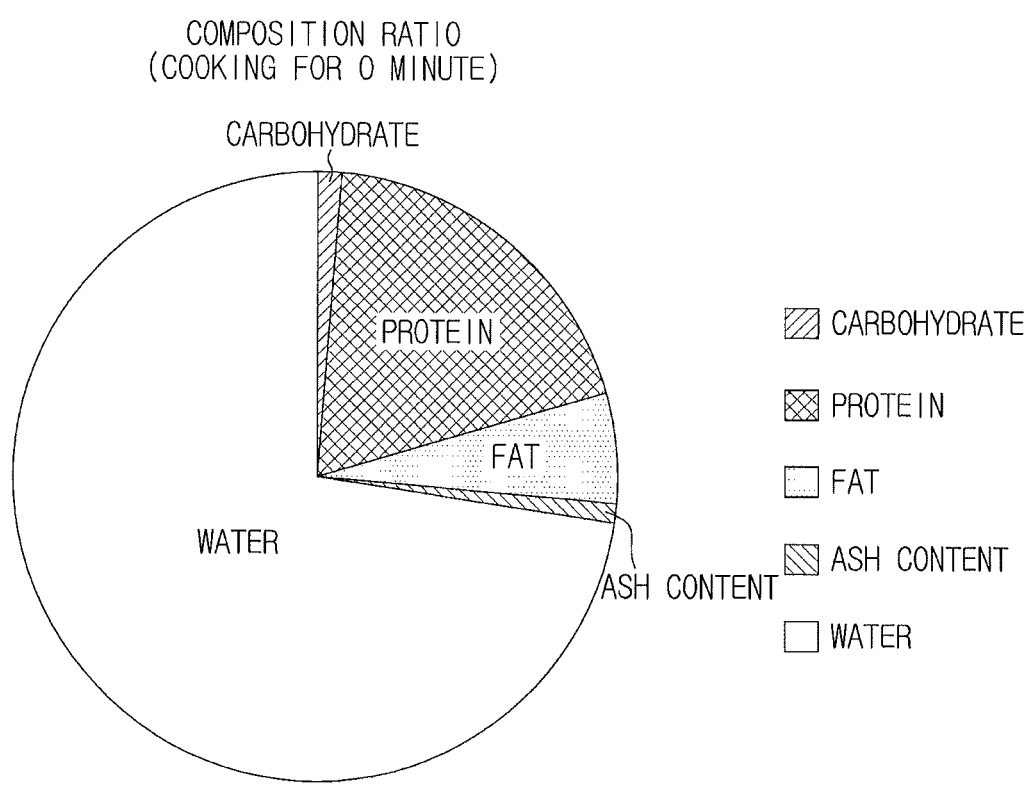
Figure 6B:
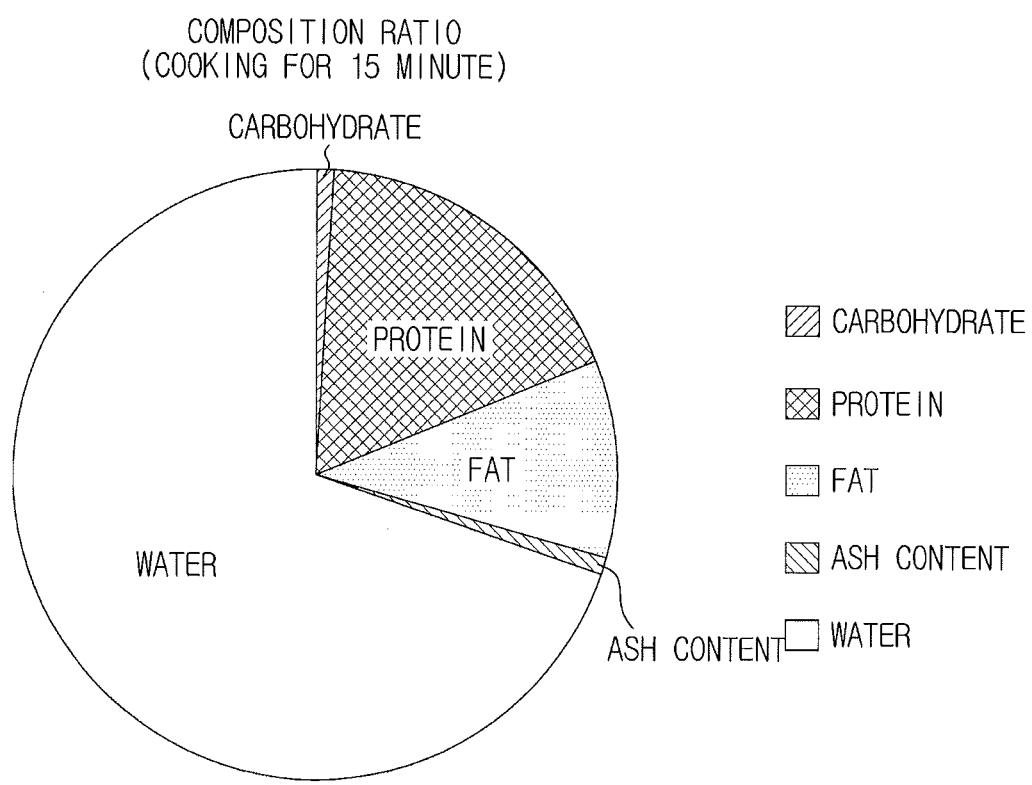
Figure 6C:
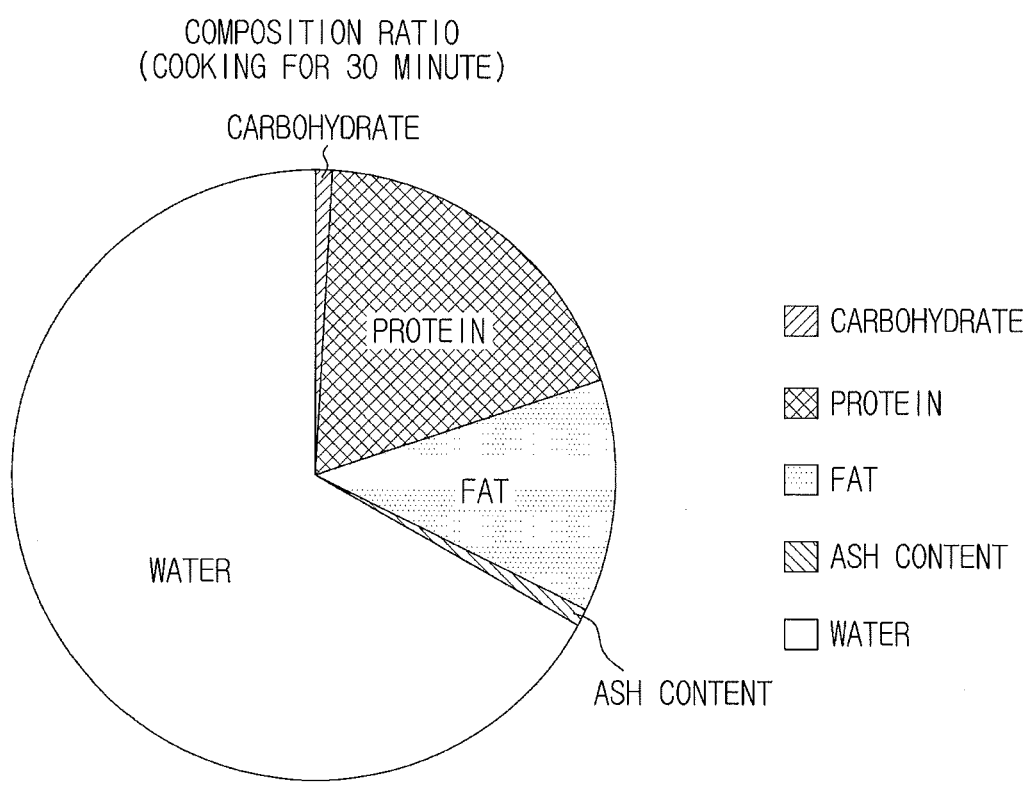

FIGS. 6A through 6D illustrate a body composition ratio that varies as cooking of the object to be heated proceeds. FIG. 6A illustrates a body composition ratio of chicken that is an object to be heated when cooking starts, and FIG. 6B illustrates a body composition ratio of chicken when 15 minutes elapse since starting cooking, and FIG. 6C illustrates a body composition ratio of chicken when 30 minutes elapse since starting cooking, and FIG. 6D illustrates a body composition ratio of chicken when 60 minutes elapse since starting cooking.

As illustrated in FIGS. 6A through 6D, the body composition ratio of chicken varies as cooking proceeds. In particular, a water ratio of chicken varies at the largest ratio as cooking proceeds. Thus, a cooking state of the object to be heated may be determined according to a change in water of the object to be heated. Thus, information regarding the change in water of the object to be heated may be obtained based on a change in impedance of the object to be heated, and the cooking state of the object to be heated may be determined based on information regarding the change in water of the object to be heated. Hereinafter, the relationship between impedance and the cooking state of the object to be heated will be described in more detail.

Figure 7:
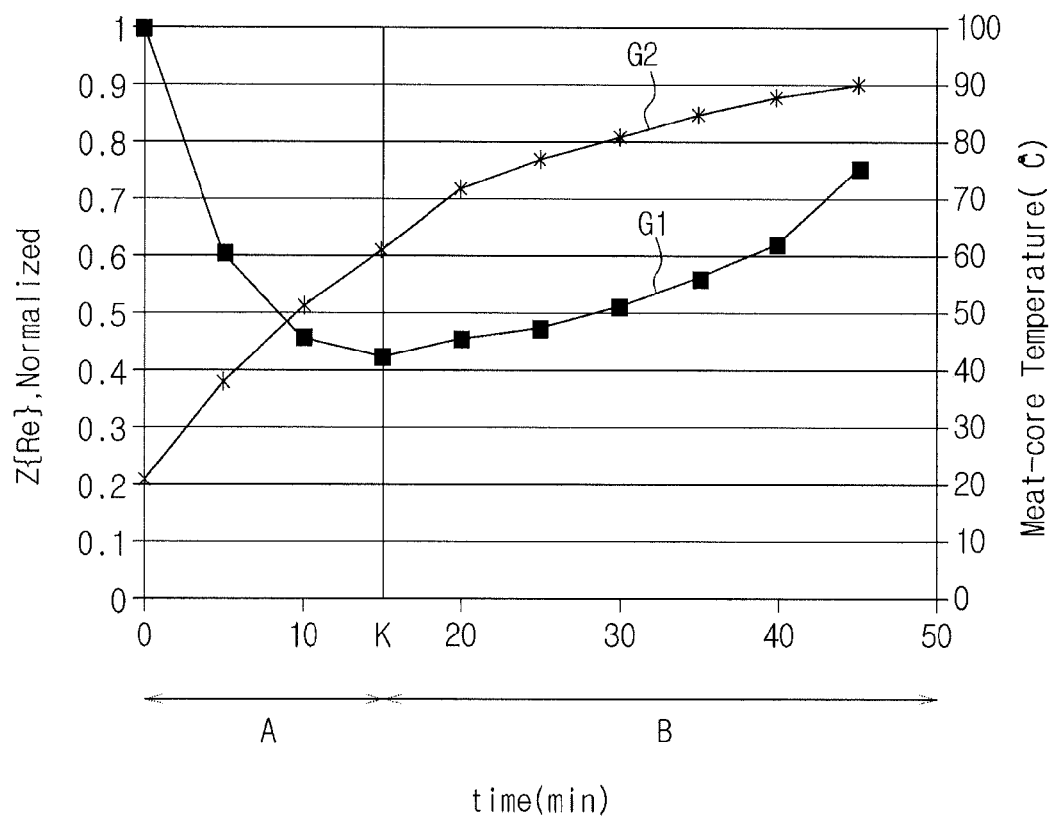
FIG. 7 is a graph showing a change in impedance versus cooking progress of the object to be heated.

FIG. 7 is a graph showing a change in impedance versus cooking progress of the object to be heated. G1 of FIG. 7 is a graph showing a change in impedance of beef that is an object to be heated, and G2 of FIG. 7 is a graph showing a change in temperature of beef that is the object to be heated. As shown in graph G1 of FIG. 7, impedance of the object to be heated varies as cooking of the object to be heated proceeds. Also, as shown in graph G2 of FIG. 7, temperature of the object to be heated increases as cooking proceeds and is converged towards a predetermined temperature if a predetermined amount of time elapses.

Impedance of the object to be heated varies as temperature of the object to be heated rises. In detail, in terms of ECW and ICW of an electrolyte component, mobility of ions increases as temperature rises. Thus, electric conductivity of water that is an electrolyte increases, and resistance values $R_{ecw}$ and $R_{icw}$ decrease, and the capacity of a capacitor is in inverse proportion to temperature. Thus, as the temperature of the object to be heated rises, impedance of the object to be heated is reduced.

Also, as cooking proceeds, water included in the object to be heated evaporates. In detail, as cooking proceeds, ICW evaporates, and a cross-sectional area of a cell is reduced, and ECW evaporates, and a distance between cells is reduced. Thus, the length of an electrical path formed with water does not vary, but an area of the electric path is reduced. In this way, when the area of the electric path through which a current can flow is reduced, the resistance values $R_{ecw}$ and $R_{icw}$ increase and thus, impedance of the object to be heated also increases.

As illustrated in graph G1 of FIG. 7, impedance of the object to be heated may be changed into a U shape according to the effects of temperature and water. In detail, a section A in which temperature of the object to be heated rises rapidly, is relatively strongly influenced by the temperature of the object to be heated so that impedance of the object to be heated is gradually reduced in the section A. Also, a section B in which water included in the object to be heated is rapidly reduced, is relatively strongly influenced by a reduction in water included in the object to be heated so that impedance of the object to be heated increases gradually.

As described above, as cooking proceeds, the temperature of the object to be heated and an amount of water included in the object to be heated vary. This change appears as a change in impedance of the object to be heated. Thus, the controller 30 may determine a cooking state of the object to be heated based on the change in impedance of the object to be heated.

Also, in this case, the controller 30 may normalize impedance of the object to be heated, so as to determine the cooking state of the object to be heated. For example, the controller 30 may normalize impedance based on impedance that is initially measured. Since the cooking state of the object to be heated is determined based on normalized impedance, the controller 30 may determine the cooking state of the object to be heated regardless of the weight or volume of the object to be heated.

Also, the controller 30 may determine the cooking state of the object to be heated based on a change in a plurality of pieces of impedance measured at different electric frequencies. As described in Equation 1 and FIG. 4, impedance of the same object to be heated may be different according to electric frequencies of voltages or currents applied to the object to be heated. Thus, a change in ICW and a change in ECW of the object to be heated may be calculated based on impedance of the object to be heated measured at different electric frequencies, and the cooking state of the object to be heated can be more delicately determined based on the change in ICW and the change in ECW.

Figure 8:
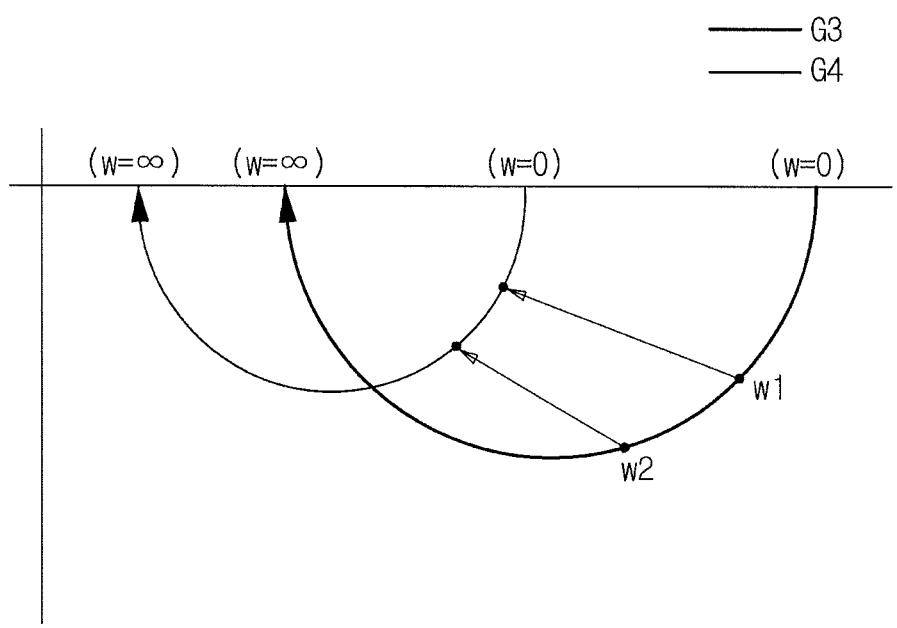
FIG. 8 is a graph showing a change in complex loci versus cooking progress of the object to be heated.

FIG. 8 is a graph showing a change in complex loci versus cooking progress of the object to be heated. A complex locus G3 of FIG. 8 is a complex locus of impedance when cooking starts, and a complex locus G4 of FIG. 8 is a complex locus of impedance after a predetermined amount of time elapses since starting cooking. In this case, as illustrated in FIG. 8, an impedance change ratio at a first electric frequency w1 and an impedance change ratio at a second electric frequency w2 are different from each other. Thus, the controller 30 may concretely calculate an amount of change in ICW and an amount of change in ECW based on a change in impedance at w1 and a change in impedance at w2. Thus, the cooking state of the object to be heated can be more accurately determined.

Meanwhile, in FIG. 8, a change in impedance is measured at two electric frequencies w1 and w2. However, embodiments of the present disclosure are not limited thereto, and the apparatus 1 for measuring the cooking state may measure a change in impedance according to at least one electric frequency determined by a user or a cooking apparatus manufacturer and may determine the cooking state of the object to be heated according to an impedance change ratio versus at least one electric frequency.

The apparatus 1 for measuring the cooking state may be provided in various cooking apparatuses and may determine the cooking state of the object to be heated that will be cooked by a cooking apparatus. Hereinafter, an oven that is an embodiment of a cooking apparatus 100 (see FIG. 9) including the apparatus 1 for measuring the cooking state, will be described. However, the cooking apparatus 100 (see FIG. 9) is not limited to the oven and may be applied to various apparatuses, such as a steam cooking apparatus that cooks an object to be heated using steam that may cook the object to be heated, and a microwave oven that cooks the object to be heated using electric waves.

Figure 9:
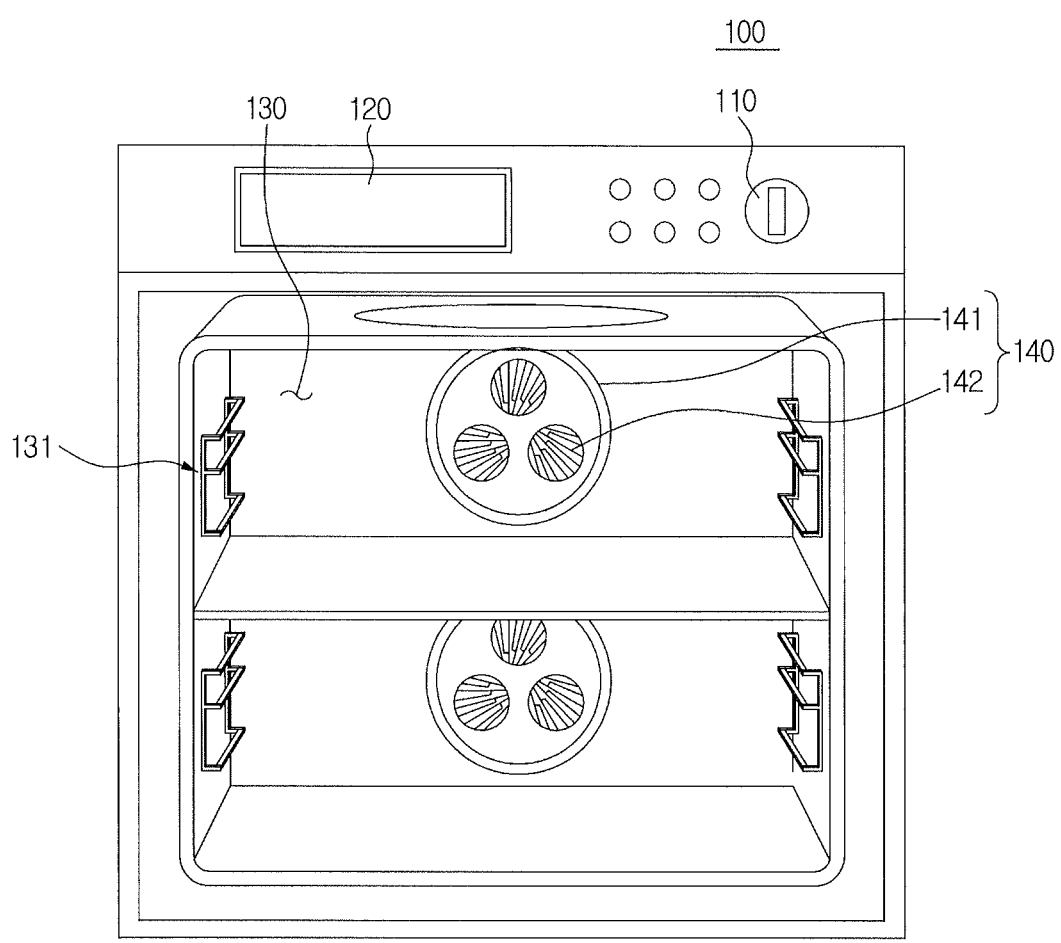
FIG. 9 is a perspective view illustrating a cooking apparatus from which a holder is taken out, in accordance with an embodiment of the present disclosure.
Figure 10:
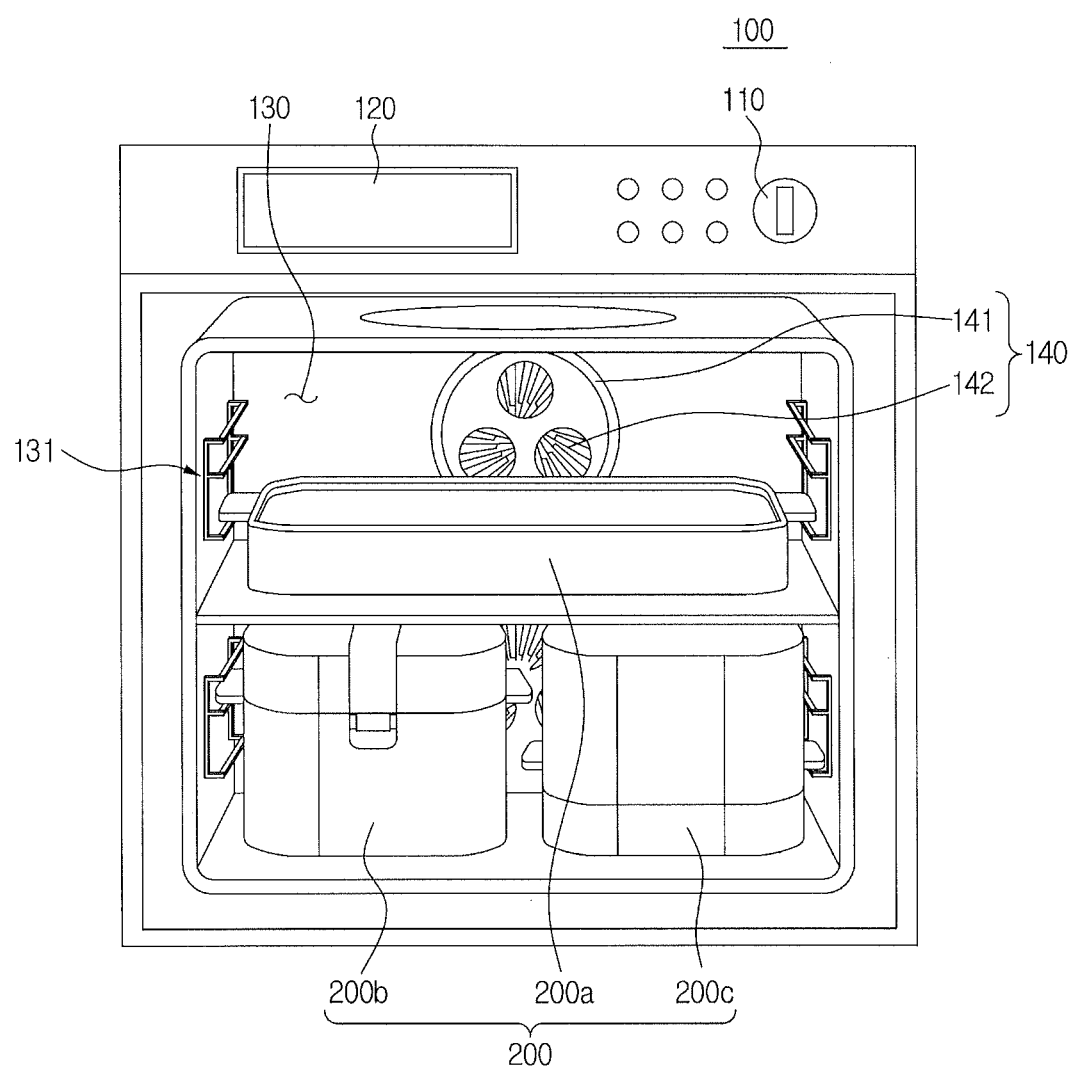
FIG. 10 is a perspective view illustrating a cooking apparatus into which the holder is inserted, in accordance with an embodiment of the present disclosure.
Figure 11:
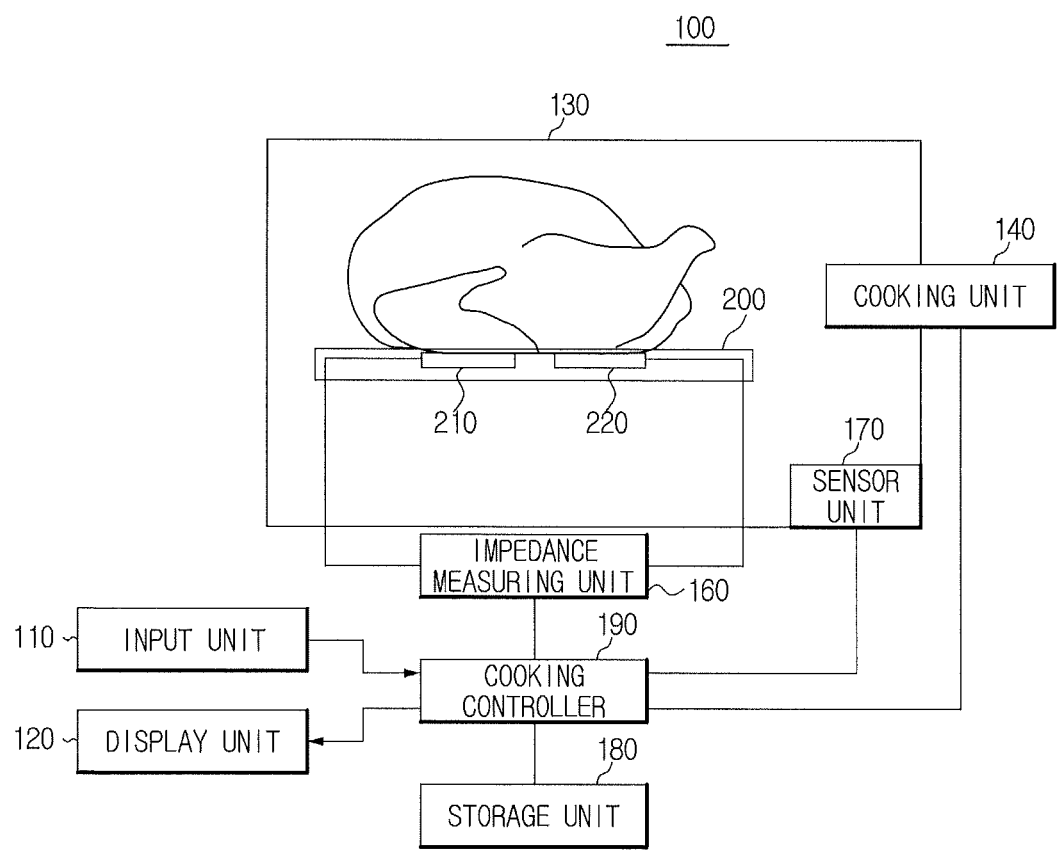
FIG. 11 is a control block diagram for describing a cooking apparatus in detail in accordance with an embodiment of the present disclosure.

FIG. 9 is a perspective view illustrating a cooking apparatus from which a holder is taken out, in accordance with an embodiment of the present disclosure, and FIG. 10 is a perspective view illustrating a cooking apparatus into which the holder is inserted, in accordance with an embodiment of the present disclosure, and FIG. 11 is a control block diagram for describing a cooking apparatus in detail in accordance with an embodiment of the present disclosure.

As illustrated in FIGS. 9 through 11, the cooking apparatus 100 includes an input unit 110 to which a control instruction of the cooking apparatus 100 is input by a user, a display unit 120 that displays information regarding the cooking apparatus 100, a cooking chamber 130 in which cooking of an object to be heated is performed, a cooking unit 140 that heats the object to be heated, an impedance measuring unit 160 that measures impedance of the object to be heated, a sensor unit 170 that measures a state of the cooking chamber 130 or the object to be heated, a storage unit 180 that stores data, and a cooking controller 190 that controls an overall operation of the cooking apparatus 100.

The control instruction of the cooking apparatus 100 is input to the input unit 110 from the user. For example, the control instruction, such as information regarding the object to be heated and a user's desired cooking state of the object to be heated, may be input to the input unit 110 from the user. The input unit 110 may be one selected from the group consisting of a joystick, a keyboard, a keypad, a touchscreen, a trackball, a mouse, and a tablet. One among them may be used as the input unit 110, and a combination of at least two among them may constitute the input unit 110.

The display unit 120 may display various information regarding the cooking apparatus 100. For example, the display unit 120 may display information regarding a cooking progress state, information regarding the state of the cooking chamber 130, and information regarding setting of the cooking apparatus 100. The display unit 120 may be implemented as one selected from the group consisting of a liquid crystal display (LCD), a light emitting diode (LED), an organic light emitting diode (OLED), an active matrix organic light emitting diode (AMOLED), a flexible display, and a three-dimensional (3D) display.

Meanwhile, when the display unit 120 is implemented as a touchscreen, the display unit 120 may perform the function of the input unit 110 in addition to its own function.

The cooking chamber 130 that is a space in which cooking of the object to be heated is performed, may be opened or sealed by a door. In this case, the cooking unit 140 for cooking the object to be heated, the sensor unit 170 for measuring the state of the cooking chamber 130, and a plurality of guide portions 131 for guiding a holder 200 including a plurality of holders 200a, 200b, and 200c may be provided at one side of the cooking chamber 130. Here, the plurality of guide portions 131 may be provided at both sides of the cooking chamber 130 to be symmetrical to each other, and the user may insert the object to be heated and the holder 200 that supports the object to be heated using the guide portions 131, as illustrated in FIG. 10.

The cooking chamber 130 may be divided into a plurality of regions, as illustrated in FIG. 9, and the plurality of holders 200a, 200b, and 200c may be inserted into the plurality of regions of the cooking chamber 130, as illustrated in FIG. 10.

The cooking unit 140 cooks the object to be heated inserted into the cooking chamber 130 according to control of the cooking controller 190. For example, the cooking unit 140 may include a heat source 141 that generates heat using electric energy, and a circulation fan 142 that circulates air inside the cooking chamber 130 using heat generated in the heat source 141.

The heat source 141 may generate heat using electric energy, and the amount of heat generated in the heat source 141 may vary according to electric energy supplied to the heat source 141. Also, the amount of electric energy supplied to the heat source 141 may be determined by the cooking controller 190.

Although the cooking apparatus 100 generates heat using electric energy, embodiments of the present disclosure are not limited thereto, and the cooking unit 140 may cook the object to be heated by generating heat using gas, by generating steam, or by generating light waves.

The impedance measuring unit 160 measures impedance of the object to be heated that contacts a first electrode portion 210 and a second electrode portion 220 that are electrically opened, as described above. The impedance measuring unit 160 may measure impedance of the object to be heated at predetermined intervals. Also, the impedance measuring unit 160 may measure impedance of the object to be heated at a predetermined frequency according to control of the cooking controller 190, may change an electric frequency of a voltage or current applied to the object to be heated and may measure a plurality of pieces of impedance of the object to be heated at different electric frequencies.

That is, the cooking apparatus 100 illustrated in FIG. 9 may measure impedance of the object to be heated by being only in contact between an outer side, e.g., an exterior, of the object to be heated via the first electrode portion 210 and the second electrode portion 220. Thus, even when an additional probe for measuring the cooking state of the object to be heated is not inserted into the object to be heated, the cooking apparatus 100 can measure the cooking state of the object to be heated. Also, the cooking apparatus 100 can measure the cooking state of the object to be heated without damage to the exterior of the object to be heated and can check an accurate cooking state regardless of a user's skill and experience.

In this case, the impedance measuring unit 160, the first electrode portion 210, and the second electrode portion 220 may be electrically connected to each other using various methods. Hereinafter, an embodiment in which an electrode and the impedance measuring unit 160 are connected to each other, will be described with reference to FIGS. 12 through 17 in detail.

Figure 12:
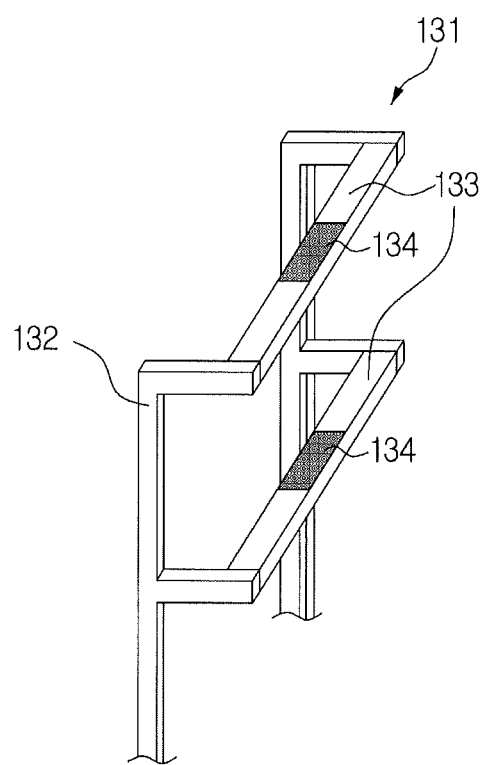
FIG. 12 illustrates an example of a guide portion.
Figure 13:
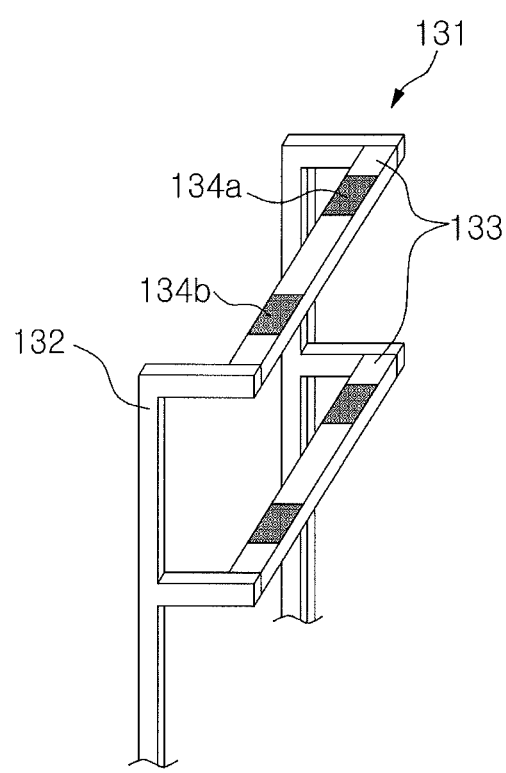
FIG. 13 illustrates another example of a guide portion.
Figure 14:
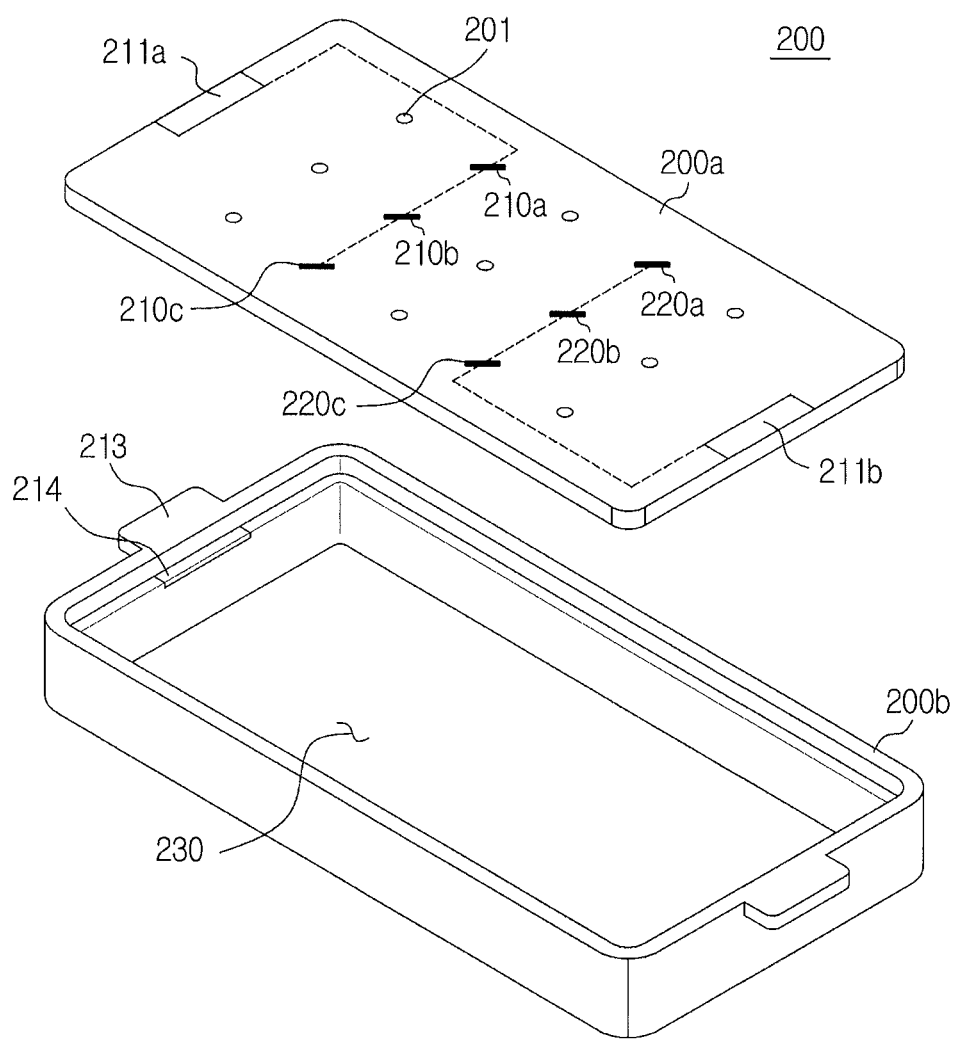
FIG. 14 is an exploded view for describing a structure of a holder in accordance with an embodiment of the present disclosure.
Figure 15:
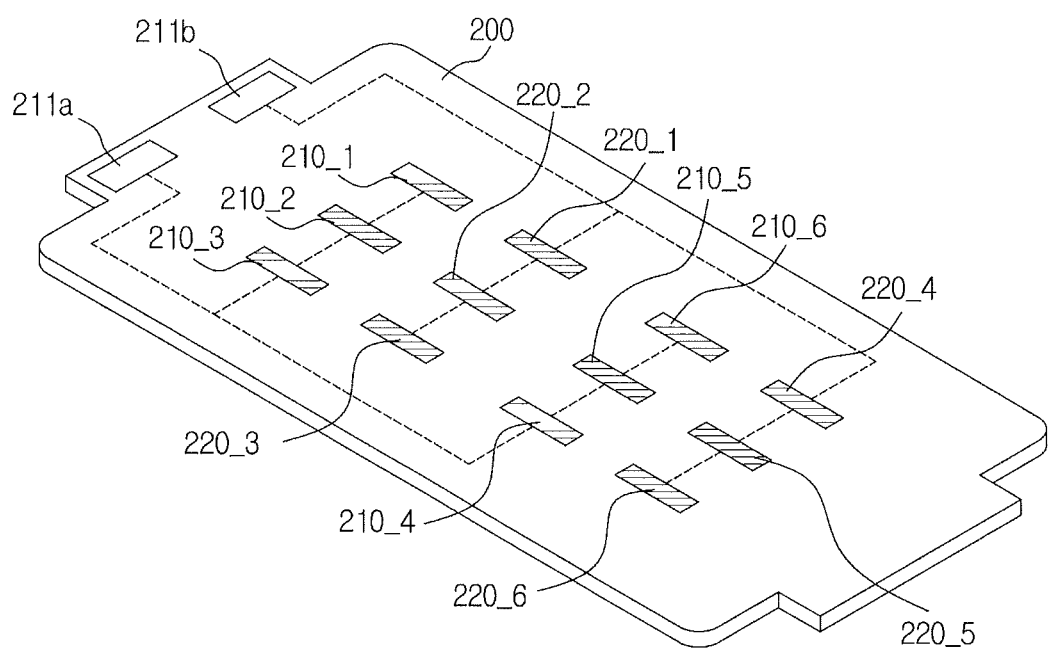
FIG. 15 illustrates a structure of a holder in accordance with another embodiment of the present disclosure.
Figure 16:
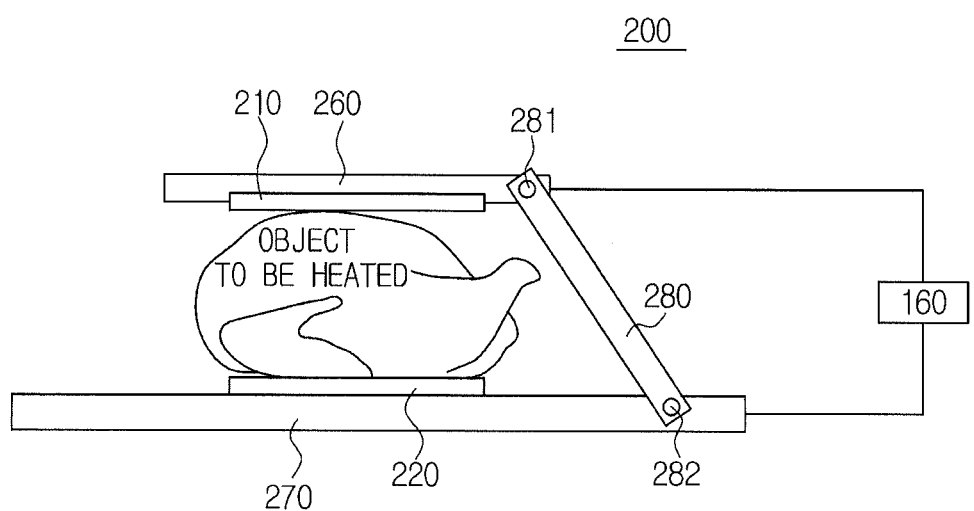
FIG. 16 illustrates a structure of a holder in accordance with still another embodiment of the present disclosure.
Figure 17:
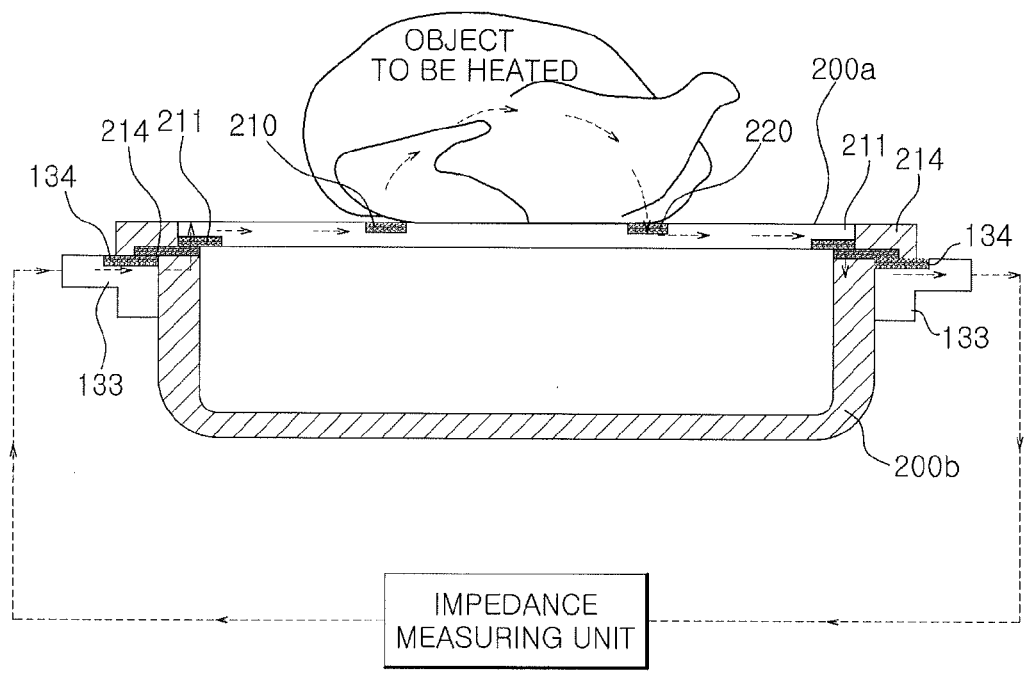
FIG. 17 schematically illustrates electrical connection between an impedance measurer and an electrode in accordance with an embodiment of the present disclosure.

FIG. 12 illustrates an example of a guide portion. FIG. 13 illustrates another example of a guide portion. FIG. 14 is an exploded view for describing a structure of a holder in accordance with an embodiment of the present disclosure. FIG. 15 illustrates a structure of a holder in accordance with another embodiment of the present disclosure. FIG. 16 illustrates a structure of a holder in accordance with still another embodiment of the present disclosure. FIG. 17 schematically illustrates electrical connection between an impedance measuring unit and an electrode in accordance with an embodiment of the present disclosure.

As illustrated in FIG. 12, each of the guide portions 131 may include rails 133 having different heights and a fixing portion 132 for fixing the rails 133 to sides of the cooking chamber 130. The user may mount the holder 200 on the rails 133, may slide the holder 200 to be inserted into the cooking chamber 130, or may slide the holder 200 inserted into the cooking chamber 130 to be taken out from the cooking chamber 130. Also, the user may select the rails 133 on which the holder 200 is to be mounted, according to the type or shape of the holder 200.

Also, a first terminal 134 may be provided on each of the rails 133 so as to apply fine electricity to the holder 200. In this case, the first terminal 134 may be electrically connected to the impedance measuring unit 160 and may be electrically insulated from the other portions of the rails 133. Also, the first terminal 134 may be formed of copper having high conductivity. Meanwhile, a guide portion 131 provided at an opposite side to one side of the cooking chamber 130 at which the guide portion 131 is provided, may also have a first terminal 134 for applying fine electricity to the holder 200 so as to correspond to the guide portion 131 illustrated in FIG. 12.

In another embodiment, as illustrated in FIG. 13, a plurality of first terminals 134a and 134b that constitute the first terminal 134 may be provided on at least one of the rails 133 of the guide portion 131. In this case, one first terminal 134a may be electrically connected to the first electrode portion 210, and the other first terminal 134b may be electrically connected to the second electrode portion 220, and when the guide portion 131 provided at one side of the cooking chamber 130 has the plurality of first terminals 134a and 134b in this way, the guide portion 131 provided at the opposite side to one side of the cooking chamber 130 may not have the first terminal 134.

The guide portion 131 illustrated in FIGS. 12 and 13 has been explained as an example of a configuration for electrical connection of the first electrode portion 210 that contacts the outer side of the object to be heated, the second electrode portion 220, and the impedance measuring unit 160. The shape or structure of the guide portion 131 is not limited thereto, and the cooking apparatus 100 may not include the guide portion 131 in a specific embodiment.

The holder 200 that supports the object to be heated may include an upper plate portion 200a that supports the object to be heated, and a housing 200b having an opening formed therein, as illustrated in FIG. 14.

The first electrode portion 210 and the second electrode portion 220 may be exposed to a front side of the upper plate portion 200a. In this case, the first electrode portion 210 may include a plurality of first electrodes 210a, 210b, and 210c that are electrically connected to one another. Also, the second electrode portion 220 may include a plurality of second electrodes 220a, 220b, and 220c that are electrically connected to one another. In order to perform electrical connection between the plurality of first electrodes 210a, 210b, and 210c and the plurality of second electrodes 220a, 220b, and 220c, a conductor may be provided inside the upper plate portion 200a or at one side of the upper plate portion 200a, as indicated by dotted lines of FIG. 14.

Furthermore, the plurality of first electrodes 210a, 210b, and 210c and the plurality of second electrodes 220a, 220b, and 220c may be disposed to be spaced apart from each other by a predetermined distance. The plurality of first electrodes 210a, 210b, and 210c and the plurality of second electrodes 220a, 220b, and 220c may be electrically insulated from each other.

Thus, when at least one of the plurality of first electrodes 210a, 210b, and 210c and the object to be heated contact each other and at least one of the plurality of second electrodes 220a, 220b, and 220c and the object to be heated contact each other, impedance of the object to be heated can be measured. In this way, the holder 200 including the first electrode portion 210 and the second electrode portion 220 is provided so as to facilitate contact between the first electrode portion 210 and the second electrode portion 220 and the object to be heated.

Also, a plurality of second terminals 211a and 211b that constitute a second terminal 211 may be provided at a lower side of the upper plate portion 200a so as to electrically connect the first electrode portion 210 and the second electrode portion 220 to the impedance measuring unit 160. In this case, the second terminal 211 may be formed of copper (Cu) having high conductivity, and the second terminal 211 and the other portions of the upper plate portion 200a may be electrically insulated from each other. Also, one second terminal 211a may be electrically connected to the first electrode portion 210, and the other second terminal 211b may be electrically connected to the second electrode portion 220.

An opening may be formed in one side of the housing 200b, and the upper plate portion 200a may be accommodated in the opening. Furthermore, an accommodation portion 230 of the housing 200b may accommodate foreign substances, such as oil or water that is discharged from the object to be heated through a plurality of through holes 201 formed in the upper plate portion 200a during a cooking operation. Thus, cleaning of the cooking apparatus 100 can be facilitated.

Also, handles 213 may be provided at both sides of the housing 200b so as to grasp the holder 200. In this case, a third terminal 214 for electrically connecting the first terminal 134 and the second terminal 211 may be provided in a position of each of the handles 213 that correspond to the first terminal 134 and the second terminal 211. In this case, the third terminal 214 contacts the first terminal 134 and the second terminal 211 and electrically connects the first electrode portion 210 and the second electrode portion 220 to the impedance measuring unit 160, as illustrated in FIG. 17. In this case, the third terminal 214 may be formed of Cu having high conductivity, and the third terminal 214 and the other portions of the upper plate portion 200a may be electrically insulated from each other.

Meanwhile, the structure of the holder 200 may vary in various ways. As illustrated in FIG. 15, the holder 200 may have only a portion for supporting the object to be heated, and the arrangement of the first electrode portion 210 and the second electrode portion 220 and the number of electrodes may also vary in various ways. That is, the plurality of second terminals 211a and 211b may be provided in positions corresponding to the first terminals 134a and 134b of a guide portion 131 illustrated in FIG. 13. In this case, one second terminal 211a may be electrically connected to a plurality of first electrodes 210_1 through 210_6, and the other second terminal 211b may be electrically connected to a plurality of second electrodes 220_1 through 220_6.

As illustrated in FIG. 16, the holder 200 may also include a first holder 260 including the first electrode portion 210, a second holder 270 including the second electrode portion 220, and a connection member 280 that connects the first holder 260 and the second holder 270. In this case, the connection member 280 may be an insulator, and the first holder 260 may be connected to a first hinge 281 of the connection member 280, and the second holder 270 may be connected to a second hinge 282 of the connection member 280. Thus, the first holder 260 may move freely by means of the first hinge 281 and the second hinge 282.

Thus, the user may move the first holder 260 so that the object to be heated can be mounted on the second holder 270 and the second electrode portion 220 and the object to be heated come into contact with each other, and the user may move the first holder 260 in a direction of the mounted object to be heated to move in a direction in which the first electrode portion 210 contact with is mounted on the object to be heated, and first electrode portion 210 the object to be heated come into contact with each other.

In this way, the first holder 260 can freely move so that the first electrode portion 210 and the second electrode portion 220 can easily contact the object to be heated. Also, as the first electrode portion 210 is placed at an upper portion of the object to be heated and the second electrode portion 220 is placed at a lower portion of the object to be heated, even when the volume of the object to be heated increases, impedance of the object to be heated can be more accurately measured.

Meanwhile, the first holder 260 illustrated in FIG. 16 has been explained as an example of a configuration that supports the object to be heated and includes the first electrode portion 210 and the second electrode portion 220 that contact an outer side of the object to be heated, and the shape or structure of the first holder 260 is not limited thereto.

As illustrated in FIG. 17, the impedance measuring unit 160 of the cooking apparatus 100 may be electrically connected to the object to be heated. In detail, the first terminal 134, the second terminal 211, and the third terminal 214 are electrically connected to one another in contact with one another. Thus, the first electrode portion 210 that is electrically connected to the first terminal 134 and the second electrode portion 220 that is electrically connected to the second terminal 211 are electrically connected to the impedance measuring unit 160.

In this case, when the first electrode portion 210 and the second electrode portion 220 are opened against each other, and when the object to be heated does not contact the first electrode portion 210 and the second electrode portion 220, they have infinite resistances. However, as illustrated in FIG. 17, when the object to be heated contacts the first electrode portion 210 and the second electrode portion 220, the first electrode portion 210 and the second electrode portion 220 are electrically connected to each other via the object to be heated.

Thus, when a voltage having a predetermined electric frequency is applied to the object to be heated, a current flows through the object to be heated, as indicated by arrows of FIG. 17. In this case, the current that flows through the object to be heated has the same electric frequency as that of a voltage applied to the object to be heated, and a magnitude of the current varies according to impedance of the object to be heated. Thus, the current applied to the object to be heated can be measured according to the above-described Ohm's law and thus, impedance of the object to be heated can be measured.

Meanwhile, FIGS. 12 through 17 illustrate examples of electrical connection of an electrode and the impedance measuring unit 160, and embodiments of the present disclosure are not limited thereto. It will be understood by one of ordinary skill in the art that any structure in which the first electrode portion 210, the second electrode portion 220, and the impedance measuring unit 160 may be electrically connected to one another, can be used.

The sensor unit 170 may detect the state of the cooking chamber 130. In detail, the sensor unit 170 may detect the state of temperature or humidity of the cooking chamber 130. For example, the sensor unit 170 may include a temperature sensor for measuring temperature of the cooking chamber 130 or the object to be heated.

The storage unit 180 may store program and data required for an operation of the cooking apparatus 100. Also, the storage unit 180 may further include an impedance database in which cooking state information according to impedance of the object to be heated is stored. In this case, the impedance database stores a cooking state according to the type of the object to be heated or the type of food and impedance of the object to be heated in each cooking state. Furthermore, as illustrated in FIG. 7, the impedance database may include information regarding passage of an inflection point K in each cooking state. In this case, the inflection point K is a point where impedance decreases and increases again. Hereinafter, the impedance database in accordance with an embodiment of the present disclosure will be described with reference to FIG. 18 in detail.

FIGS. 18A through 18C are views for describing an impedance database in accordance with an embodiment of the present disclosure. FIG. 18A illustrates a change in impedance according to a cooking state of beef, and FIG. 18B illustrates a change in impedance according to a cooking state of pork, and FIG. 18C illustrates a change in impedance according to a cooking state of chicken.

As illustrated in FIGS. 18A through 18C, the impedance database stores impedance according to a cooking state of various objects to be heated that may be cooked by the cooking apparatus 100. In this case, the impedance according to the cooking state may be obtained by experiments, statistics, or a rule of thumb. Also, impedance according to the cooking state may be normalized impedance. For example, as illustrated in FIG. 18, normalized impedance may be stored in each cooking state based on impedance generated when cooking starts.

Furthermore, the impedance database may store additional factors that may be used to determine the cooking state of the object to be heated, such as temperature of the object to be heated or passage of an inflection point, in addition to impedance according to the cooking state. In this case, the inflection point is a point where impedance decreases and increases again, as illustrated in FIG. 7.

The cooking controller 190 controls the overall operation of the cooking apparatus 100 so that the object to be heated can be cooked in a predetermined cooking state. The cooking controller 190 may correspond to one or a plurality of processors. In this case, the processor may be implemented as an array of a plurality of logic gates or as a combination of memories in which a general-use microprocessor and a program that may be executed by the microprocessor are stored. Also, it will be understood by one of ordinary skill in the art that the processor may be implemented as hardware having other types.

The cooking controller 190 may cook the object to be heated by driving the cooking unit 140. Also, the cooking controller 190 may determine the cooking state of the object to be heated based on impedance measured by the impedance measuring unit 160. In this case, if it is determined that the determined cooking state of the object to be heated is a cooking state set by the user, the cooking controller 190 may finish cooking and may inform the user of completion of cooking.

Also, the cooking controller 190 may normalize impedance measured by the impedance measuring unit 160. In this way, a change in impedance of the object to be heated is normalized so that the cooking state of the object to be heated can be determined regardless of the weight or volume of the object to be heated.

Also, the cooking controller 190 may determine the cooking state of the object to be heated based on information regarding the cooking state according to impedance stored in the impedance database. For example, referring to FIG. 18A, when a relative value of normalized impedance is 0.42 based on impedance that is initially measured, the cooking controller 190 may determine that a cooking state of beef that is the object to be heated is rare.

Also, the cooking controller 190 may determine a degree of cooking of the object to be heated in consideration of other factors in addition to the change in impedance of the object to be heated. In this case, it will be understood by one of ordinary skill in the art that other factors include all types of factors that may affect the cooking state of the object to be heated, such as passage of the inflection point in which impedance decreases and increases again, temperature of the object to be heated, temperature of the cooking chamber 130, and humidity of the cooking chamber 130. These factors may be detected by the sensor unit 170.

In an embodiment, as illustrated in FIG. 7, impedance of the object to be heated gradually decreases and gradually increases again in case of passage of the inflection point K. Thus, a plurality of values having the same impedance may be present. Thus, the cooking controller 190 may determine the cooking state of the object to be heated in consideration of both the change in impedance of the object to be heated and passage of the inflection point K.

For example, referring to FIG. 18A, if impedance normalized based on initially-measured impedance since passage of the inflection point K is 0.45, the cooking controller 190 may determine that the cooking state of beef that is the object to be heated is medium.

Also, the cooking controller 190 may determine the cooking state of the object to be heated based on a change in a plurality of pieces of impedance measured at different electric frequencies. To this end, the above-described impedance database may store information regarding the cooking state of the object to be heated according to the change in impedance of the object to be heated at different electric frequencies. Since the cooking state of the object to be heated is determined based on the change in the plurality of pieces of impedance measured at different electric frequencies in this way, the cooking apparatus 100 may determine the cooking state of the object to be heated more accurately.

Figure 19:
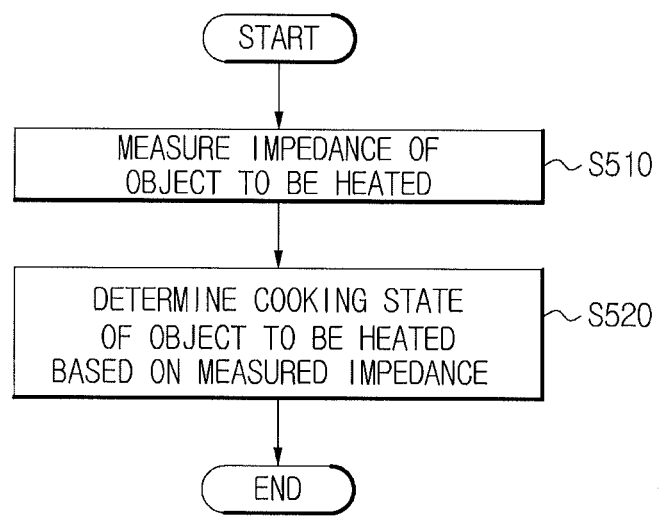
FIG. 19 is a flowchart illustrating a method of controlling a cooking apparatus in accordance with an embodiment of the present disclosure.

FIG. 19 is a flowchart illustrating a method of controlling a cooking apparatus in accordance with an embodiment of the present disclosure.

As illustrated in FIG. 19, the cooking apparatus 100 measures impedance of the object to be heated (S510). In this case, the object to be heated may be placed between the first electrode portion 210 and the second electrode portion 220 that are opened against with each other, and the first electrode portion 210 and the second electrode portion 220 may be electrically connected to each other via the object to be heated. In detail, the cooking apparatus 100 may measure impedance of the object to be heated based on the Ohm's law. To this end, the cooking apparatus 100 may apply a current or voltage having a predetermined electric frequency to the object to be heated and may measure the voltage or current applied to the object to be heated.

Also, the cooking apparatus 100 may apply currents or voltages having different electric frequencies to the object to be heated and may measure a plurality of pieces of impedance according to the electric frequencies.

The cooking apparatus 100 may determine a cooking state of the object to be heated based on measured impedance (S520). As described above, impedance of the object to be heated varies according to a change in temperature and water as cooking proceeds. Thus, the cooking apparatus 100 may determine the cooking state of the object to be heated based on impedance of the object to be heated. Hereinafter, an operation of determining the cooking state of the object to be heated will be described with reference to FIG. 20 in more detail.

Figure 20:
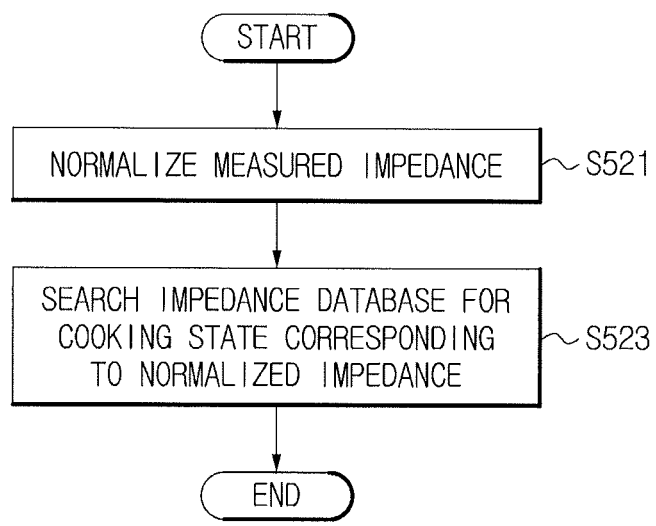
FIG. 20 is a flowchart illustrating Operation S520 of FIG. 19 in more detail.

FIG. 20 is a flowchart illustrating Operation S520 of FIG. 19 in more detail. As illustrated in FIG. 20, the cooking apparatus 100 normalizes impedance of the object to be heated measured in Operation S510 (S521). In this way, the cooking state of the object to be heated may be determined by normalizing impedance of the object to be heated so that the cooking state of the object to be heated can be determined regardless of the size, volume, and weight of the object to be heated.

Impedance of the object to be heated may be normalized in various ways. For example, impedance of the object to be heated may be normalized based on a value of impedance of the object to be heated measured when cooking starts.

The cooking apparatus 100 searches an impedance database for a cooking state corresponding to normalized impedance (S523). In this case, the impedance database may include information regarding a cooking state according to the type of the object to be heated or the type of food, impedance of the object to be heated in each cooking state, passage of an inflection point in each cooking state, and temperature of the object to be heated in each cooking state.

Meanwhile, the cooking apparatus 100 searches the impedance database for a cooking state corresponding to normalized impedance in consideration of factors other than normalized impedance. For example, the cooking apparatus 100 may also search the cooking state of the object to be heated in consideration of normalized impedance in addition to factors, such as passage of the inflection point, temperature of the object to be heated, temperature of the cooking chamber 130, and a cooking time.

Also, the cooking apparatus 100 may determine the cooking state of the object to be heated based on a change in a plurality of pieces of impedance measured at different electric frequencies. To this end, the above-described impedance database may store information regarding the cooking state of the object to be heated according to the change of impedance of the object to be heated at different electric frequencies.

Figure 21:
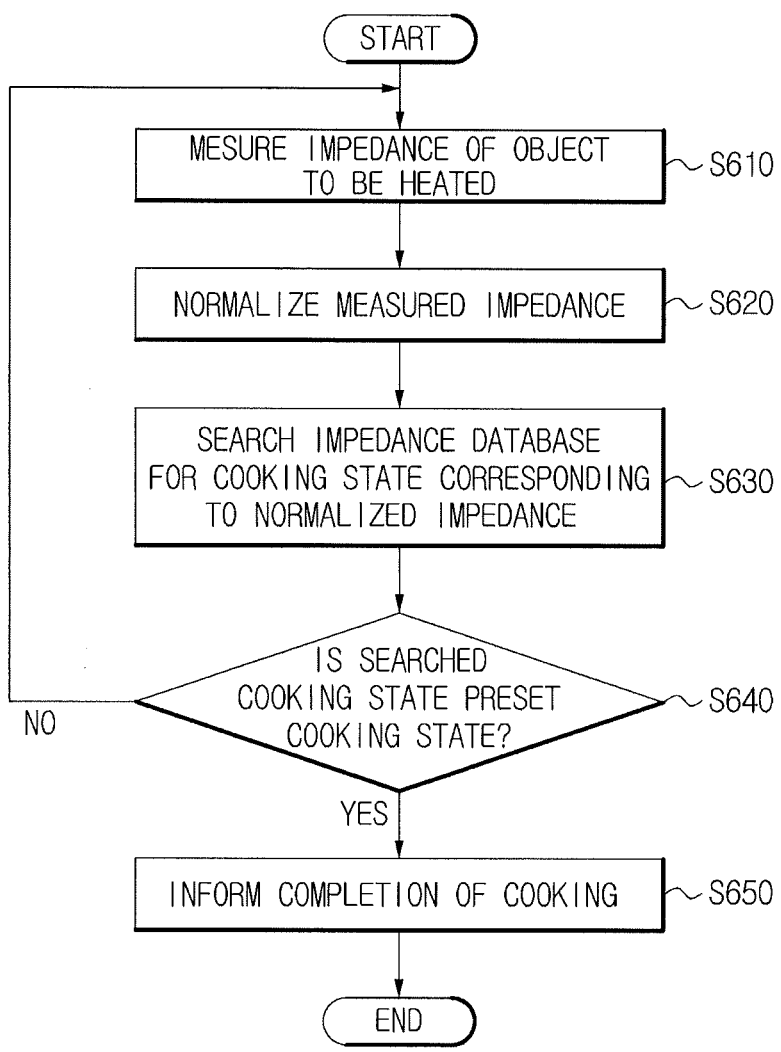
FIG. 21 is a flowchart illustrating a method of controlling a cooking apparatus in accordance with another embodiment of the present disclosure.

FIG. 21 is a flowchart illustrating a method of controlling a cooking apparatus in accordance with another embodiment of the present disclosure.

As illustrated in FIG. 21, the cooking apparatus 100 may measure impedance of the object to be heated (S610) and may normalize measured impedance (S620).

The cooking apparatus 100 may search an impedance database for a cooking state corresponding to normalized impedance (S630) and may determine whether the searched cooking state is the same as a preset cooking state (S640). In this case, the preset cooking state may be a cooking state selected by the user. In this case, information regarding the object to be heated may also be input to the cooking apparatus 100 from the user.

If the searched cooking state is not the same as the preset cooking state (NO of S640), the cooking apparatus 100 may measure impedance of the object to be heated again since a predetermined amount of time elapses (S610).

On the other hand, if the searched cooking state is the same as the preset cooking state (YES of S640), the cooking apparatus 100 may inform the user of completion of cooking (S650) and may finish cooking of the object to be heated.

As described above, in a cooking apparatus and a method of controlling the cooking apparatus according to the one or more embodiments of the present disclosure, a cooking state of an object to be heated can be accurately determined.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A cooking apparatus comprising:
a holder to support an object to be heated, the holder comprising a first electrode portion and a second electrode portion; and
a guide portion to support the holder;
an impedance measurer configured to, while the first electrode portion and the second electrode portion are placed outside of, and in contact with an outer surface of, the object to be heated by the cooking apparatus, and are spaced apart from each other by a predetermined distance, measure an impedance of the object to be heated by applying electricity to the first electrode portion and the second electrode portion;
a controller to determine a cooking state of the object to be heated based on the measured impedance,
wherein:
the first electrode portion and the second electrode portion are electrically connected to the impedance measurer;
the guide portion comprises a pair of first terminals that are connected to the impedance measurer; and
the holder comprises a pair of second terminals that are connected to the first electrode portion and the second electrode portion and that are formed in positions corresponding to the pair of first terminals.

2. The cooking apparatus of claim 1, wherein the impedance measurer comprises:
a voltage source to apply a voltage having a predetermined electric frequency to the object to be heated; and
an amperemeter to detect a current applied to the object to be heated.

3. The cooking apparatus of claim 1, wherein the impedance measurer comprises:
a current source to apply a current having a predetermined electric frequency to the object to be heated; and
a voltmeter to detect a voltage applied to the object to be heated.

4. The cooking apparatus of claim 1, wherein the first electrode portion comprises a plurality of first electrodes electrically connected to each other, and the second electrode portion comprises a plurality of second electrodes electrically connected to each other.

5. The cooking apparatus of claim 1, further comprising an impedance database in which impedance of the object to be heated according to the cooking state is stored.

6. The cooking apparatus of claim 5, wherein the impedance database stores additional factors according to the cooking state.

7. The cooking apparatus of claim 6, wherein the additional factors comprise at least one of a passage of an inflection point in which impedance decreases and increases again, temperature of the object to be heated, and temperature of a cooking chamber.

8. The cooking apparatus of claim 5, wherein the controller searches the impedance database for a cooking state corresponding to the measured impedance.

9. The cooking apparatus of claim 1, wherein the controller normalizes the measured impedance, converts the impedance into normalized impedance, and determines a cooking state of the object to be heated based on the normalized impedance.

10. The cooking apparatus of claim 9, wherein the normalized impedance is converted based on impedance of the object to be heated measured in a cooking initial state.

11. The cooking apparatus of claim 1, wherein the controller finishes cooking of the object to be heated when the cooking state is a preset cooking state.

12. The cooking apparatus of claim 1, wherein the holder further comprises:
   a first holder comprising the first electrode portion, the first holder to contact an upper portion of the object to be heated;
   a second holder comprising the second electrode portion, the second holder to support a lower portion of the object to be heated; and
   a connection member to connect the first holder and the second holder so that the first holder is capable of moving.

13. The cooking apparatus of claim 1, wherein the holder further comprises:
   an upper plate portion comprising the first electrode portion, the second electrode portion, and a plurality of through holes formed therein; and
   a housing comprising an opening formed in one side thereof, the upper plate portion being accommodated in the opening, the housing to accommodate foreign substances discharged through the plurality of through holes.

14. The cooking apparatus of claim 13, wherein the upper plate portion further comprises the pair of second terminals, and
   the housing further comprises a pair of third terminals that are formed in positions corresponding to the pair of second terminals.

15. The cooking apparatus of claim 14, further comprising a guide portion to support the housing,
   wherein the guide portion comprises the pair of first terminals, the pair of first terminals formed in positions corresponding to the pair of third terminals, and
   the first electrode portion and the second electrode portion are electrically connected to the impedance measurer.

16. The cooking apparatus of claim 1, wherein the impedance measurer measures a plurality of impedance values of the object to be heated at different electric frequencies, and
   the controller determines a cooking state of the object to be heated based on the plurality of the impedance values of the object to be heated.

* * * * *